(12) United States Patent
Phaneuf et al.

(10) Patent No.: US 6,592,885 B2
(45) Date of Patent: Jul. 15, 2003

(54) METHOD FOR MAKING INFECTION-RESISTANT FABRICATED TEXTILE ARTICLES FOR BIOMEDICAL APPLICATIONS

(76) Inventors: Matthew D. Phaneuf, 29 Oak St., Ashland, MA (US) 01721; William C. Quist, 125 Pleasant St., Brookline, MA (US) 02446; Martin J. Bide, 256 Willard Ave., Wakefield, RI (US) 02879; Frank W. LoGerfo, 155 Lewis Rd., Belmont, MA (US) 02478

( * ) Notice: Subject to any disclaimer, the term of this patent is extended or adjusted under 35 U.S.C. 154(b) by 0 days.

(21) Appl. No.: 09/876,604

(22) Filed: Jun. 7, 2001

(65) Prior Publication Data

US 2003/0091616 A1 May 15, 2003

(51) Int. Cl.[7] .................. A01N 25/34; A61F 13/00; A61F 2/00; A61K 9/14
(52) U.S. Cl. ................ 424/404; 424/402; 424/422; 424/423; 424/449; 424/443; 424/484
(58) Field of Search .................. 424/422, 423, 424/449, 443, 402, 484

(56) References Cited

U.S. PATENT DOCUMENTS 3,875,937 A * 4/1975 Schmitt et al. ........ 128/DIG. 8
5,281,662 A * 1/1994 Ito et al. .................. 525/383

* cited by examiner

*Primary Examiner*—Thurman K. Page
*Assistant Examiner*—Isis Ghali
(74) *Attorney, Agent, or Firm*—David Prashker (57) ABSTRACT

The present invention provides a method for making an infection-resistant fabricated textile article which is suitable for any in-vivo usage either as a topical bandage, on an implantable configured construct, or as part of a prosthetic mechanical appliance. The method of manufacture applies broadly to any and all fabrics, cloths, gauzes, and/or films comprised in whole or in part of fibers; and provides an infection-resistant textile of valued use in a wide range and variety of medical applications.

14 Claims, 6 Drawing Sheets

METHOD FOR MAKING INFECTION-RESISTANT FABRICATED TEXTILE ARTICLES FOR BIOMEDICAL APPLICATIONS

RESEARCH SUPPORT

Research support for the present invention was provided in part by Grant No. 2-R01-21796-8 from the National Institutes for Health, National Heart, Lung and Blood Institute. The U.S. government has certain rights in the invention.

BACKGROUND OF THE INVENTION

Any penetration of the skin carries with it the risk of potential infection. This risk pertains to simple wounds incurred by accident or negligence; to surgical procedures performed under controlled conditions which utilize different biomaterials for the closure and dressing of incisions and/or wounds; and to a diverse range of in-vivo implantable textile fabrics, configured textile articles, and textile-containing mechanical appliances and devices which are surgically introduced into the body for diagnostic, therapeutic and/or prosthetic purposes.

The rational use of antimicrobial agents against infection, particularly for simple wound treatment, has been advocated generally and has been previously reviewed in detail [Rodgers, K. G., *Emer. Med. Clin. N. Am.* 10: 753 (1992)]. Similarly, the major concerns regarding the ever-growing incidence of infections resulting from biocompatible textiles, articles and devices implanted in the body—espite recent advances in sterile procedures used in the clinical/surgical setting—have been considered and reviewed as the primary purpose and focus of a FDA/EPA/CDC/AAMI joint conference [Proceedings, Infection Control Symposium: Influence Of Medical Device Design, U.S. Dept. of Health and Human Services, Bethesda, Md., January 1995]. Moreover, the use of antibiotics and of mechanisms for delivering antimicrobial agents generally, particularly via slow-release delivery systems over time, to prevent or reduce severity of infection for implanted biodegradable materials has been reviewed [Sasmor et al., *J. Vasc. Sur.* 14: 521 (1993)]. All of these considerations lead to the same conclusion: Infection, with or without the use of antibiotics, must be prevented or be controlled for all implantable biomaterials (including textiles, articles and devices) regardless of need or medical purpose.

Infection of Implantable Biomaterials

Infection of implantable biomaterials, specifically prosthetic vascular grafts, is an ever-growing problem and concern. For example, prosthetic vascular grafts, which are composed primarily of either polyester or polytetrafluoroethylene (PTFE), are a source of significant clinical morbidity and mortality upon infection [Goldstone, J. and W. S. Moore, *Am. J. Surg.* 128: 225 (1974); Liekweg et al., *Surgery* 81: 335 (1977); Bunt, T. J., *Surgery* 93: 733 (1983); Golan, J. F., *Infect. Dis. Clin. N. Am.*, 3: 247 (1989); Sugarman, B. and E. J. Young, *Infect. Dis. Clin. N. Am.* 3: 187 (1989)], significantly impacting patient quality of life. Graft infection occurs in 2–6% of all clean cases performed [Hoffert et al., *Arch. Surg.* 90: 427 (1965); Fry, W. L. and S. M. Lindenauer, *Arch. Surg.* 94: 600 (1966); Rittenhouse et al. *Ann. Surg.* 170: 87 (1969); Drapanas et al., *Ann. Surg.* 172: 351 (1970); Szilagyi et al., *Ann. Surg.* 176: 321 (1972)], with morbidity and mortality related to the anatomic position of the graft. Infectious inoculation of the biomaterial presumably occurs at the time of implantation or as a result of transient bacteremia in the immediate post-operative period [Cheri et al., *J. Vasc. Surg.* 14: 521 (1991)]. Perioperative parental antibiotics, while having a defined role in wound infection prophylaxis, often fail to permeate the avascular spaces immediately around prosthetic grafts as well as the carbohydrate-rich bacterial biofilm once pathogens have adhered [Gristina, A. G., *Science* 237: 1585 (1987); Kaiser et al., *Ann. Surg.* 188: 283 (1978); Greco, R. S., *J. Vasc. Surg.* 13: 5 (1991); Bandyk et al., *J. Vasc. Surg.* 13: 575 (1991)].

The two main types of bacteria responsible for graft infection are the coagulase negative *Staphylococcus aureus* (*S. aureus*) and *Staphylococcus epidermidis* (*S. epidermidis*). *S. aureus* has been shown to be responsible for 65–100% of acute (days to weeks) infections (3,14). Typically, these infections develop rapidly and generate an intense response by the host defense mechanisms. An ever-increasing problem (which has been documented both in animal models and in humans) is the susceptibility of vascular prostheses to later (months to years) infection. *S. epidermidis* has emerged as the leading isolate from infection vascular conduits (20–60%) with infection appearing late after implantation. Both of these instances are clearly not affected by low level antibiotic transiently occurring at the time of surgery. A decreased amount of antibiotic may also play a role in the development of resistant organisms.

Health care costs for graft infection should also be considered since the onset of this complication results in elevated patient care costs. In 1989, approximately $150M was spent on the implantation of synthetic arterial grafts in the United States. Using the estimated infection rates, approximately $3 to $9 million has been spent to implant another vascular graft external of the infection site, a procedure required to prevent subsequent infection and failure of the replacement graft. The cost of treating infection, the mortality that occurs in some 25% of infected cases and inflation also must be included. Thus, the overall total impact of graft infection on health care costs can only be estimated, however, the magnitude of the problem is extremely significant, driving the research to develop infection-resistant biomaterials.

Conventional Efforts To Combat Graft Surface Infections

Numerous strategies have been attempted in order to create an infection-resistant graft surface for biomaterials. Chelating agents have been evaluated as a release system for antibiotics from a biomaterial surface. One approach which has been the subject of numerous investigations was the ionic binding of antibiotics by surfactants. Cationic surfactants such as tridodecylmethyl ammonium chloride and benzalkonium chloride were sorbed at the anionic surface potential of a polymeric material, thereby permitting weak adhesion of anionic antibiotics to the surface [Harvey et al., *Ann. Surg.* 194: 642 (1981); Harvey et al., *Surgery* 92: 504 (1982); Harvey et al., *Am. J. Surg.* 147: 205 (1984); Shue et al., *J. Vasc. Surg.* 8: 600 (1988); Webb et al., *J. Vasc. Sur.* 4: 16 (1956)]. The selected antibiotic was then released upon contact with blood. Silver was also examined as a release system for various antibiotics from graft surfaces, applied either as a chelating agent [Modak et al., *Surg. Gynecol. Obstet.* 164: 143 (1987); Benvenisty et al., *J. Surg. Res.* 44: 1 (1988); White et al., *J. Vasc. Surg.* 1: 372 (1984)] or alone due to its antimicrobial properties.

Binding agents have also been employed in order to create localized concentrations of antibiotic on the graft surface. These agents, which were either protein or synthetic-based, were embedded within the biomaterial matrix thereby either "trapping" or ionically binding the antibiotic. The basement membrane protein collagen has served as a release system for rifampin, demonstrating antimicrobial efficacy in a bacteremic challenge dog model [Krajicek et al., *J. Cardiovasc. Surg.* 10: 453 (1969)] as well as in early European clinical trials [Goeau-Brissonniere, O., *J. Mal. Vasc.* 21: 146 (1996); Strachan et al., *Eur. J. Vasc. Surg.* 5: 627 (1991)]. Fibrin, either as a pre-formed glue or in pre-clotted blood, has been utilized as a binding agent for various antibiotics including gentamycin, rifampin and tobramycin [Haverich et al., *J. Vasc. Surg.* 14: 187 (1992); McDougal et al., *J. Vasc. Surg.* 4: 5 (1986); Powell et al., *Surgery* 94: 765 (1983); Greco et al., *J. Biomed. Mater. Res.* 25: 39 (1991)].

Levofloxacin has been incorporated in an albumin matrix and gelatin has been used as the release system for the antibiotics rifampin and vancomycin, with animal studies also showing efficacy in acute bacteremic challenges [Muhl et al., *Ann. Vasc. Surg.* 10: 244 (1996); Sandelic et al., *Cardiovasc. Surg.* 4: 389 (1990)].

Synthetic binders have also been evaluated for antibiotic release as a replacement for the protein binders. Some synthetic binders were incorporated directly into the biomaterial matrix, in a similar fashion as the protein binders, permitting sustained release of a selected antibiotic over time [Shenk et al., *J. Surg. Res.* 47: 487 (1989)]. Recent techniques also have utilized these types of binder materials as a scaffolding to covalently bind antibiotics to the biomaterial surface [Suzuki et al., *ASAIO J*. 43: M854 (1997)]. Release of the antimicrobial agent was controlled by bacterial adhesion to the surface which resulted in antibiotic cleavage. This method promotes "bacterial suicide" while maintaining antibiotic, which is not needed to prevent infection, localized on the surface. Other techniques have involved incorporating the antibiotic either into the synthesis process of the polymer [Golomb et al., *J. Biomed. Mater. Res.* 25: 937 (1991); Whalen et al., ASAIO J. 43: M842 (1997)], or by embedding the antibiotic directly into the interstices of the material [Okahara et al., *Eur. J. Vasc. Endovasc. Surg.* 9: 408 (1995)].

There are several drawbacks for each of these technologies. For the chelation agents, 50% of the antibiotic has been shown to elute from the graft surface within 48 hours, with less than 5% remaining after three weeks [Greco et al., *Arch. Surg*2. 120: 71 (1985)]. While this antibiotic coverage is adequate for small localized contaminations, large infectious inoculums are not addressed. For the binding agents, antibiotic release may be quite varied depending on the rate of binder degradation or binder release from a surface which is under high shear stress from blood flow. Comparably, both types of surface modifications rely on exogenous matter which may affect the overall healing of the graft surface, either by releasing toxic moieties or by promoting thrombogenesis. Thus, these potential complications have accentuated the need to create an infection-resistant graft surface which is devoid of exogenous matter such as binding agents.

Use Of Antibiotics As Dyes

Noticeably, all of the above identified reported investigations avoid the examination of any direct material/antibiotic interaction. Some attempts to use direct interactions, particularly dye-fiber interactions as a model, in order to provide infection resistance without exogenous binders have been recently made. Antibiotic release is essential, unlike proteins which are still active when covalently bound. Moreover, dyes have substantivity; and will "exhaust" from a bath preferentially into a fiber, when attracted by physical forces of attraction.

Initial efforts in this regard examined the use of commercially available dyes as anchors for antibiotic molecules, and even determined the antibiotic activity of some dyes [see for example: U.S. Pat. No. 5,281,662; and Bide et al., *Textile Chemist and Colorist* 25: 15–19 (1993). This approach was unrewarding. In contrast, the direct use of antibiotics was examined [Phaneuf et al., *J. Biomed. Mat. Res.* 27: 233–237 (1993); Ozaki et al., *J. Surg. Res.* 55: 543–547 (1993); Phaneuf et al., in *Antimicrobial/Anti-Infective Materials* (Sawan, S. P. and G. Manivannan, editors), Chap. 10, pp. 239–259 (2000); and the references cited within each of these printed publications]. Fluoroquinolone antibiotics are particularly suitable in such applications. They are stable to dry heat and to hot aqueous media; they have an appropriate molecular size, and (in the absence of any reliable method for predicting physical interactions) a somewhat dye-like structure. Two of the most common commercial quinolones which are currently available are Ciprofloxacin (Cipro) and Ofloxacin (Oflox).

Despite all these developments there remains a recognized and continuing need for further improvements in the making of infection-resistant, biomedical materials, devices and configured constructs formed of textile fibers. All such improvements in the making and/or preparation of implantable, textile fiber containing articles of manufacture which could resist microbial infections and inhibit microbial growth would be seen as a crucial advantage and outstanding benefit in this medical field.

SUMMARY OF THE INVENTION

The present invention is a major advance in the development of biomedical materials, devices and constructs which are infection resistant. Accordingly, the invention may be used in a wide range of different in-vivo medical, biomedical, and prosthetic applications; and may be summarized as:

A method for making an infection-resistant fabricated textile article useful for biomedical applications in-vivo, said method comprising the steps of:
   obtaining a fabricated textile article comprised of at least one type of fiber or fabric matrices able to take up aqueous fluids;
   preparing an aqueous antibiotic fluid of predetermined concentration comprising water and at least one water-miscible antibiotic composition which has characteristic antimicrobial properties, is heat stable and has a relative molecular mass in the 300–1500 range;
   perfusing said prepared antibiotic fluid across said fibers or fabric matrices of said fabricated textile article for a prechosen period of time such that said prepared antibiotic fluid permeates into at least some of the fibers or fabric matrices comprising said fabricated textile article;
   allowing said antibiotic perfused fabricated textile article to dry; and
   heating said dried, antibiotic perfused fabricated textile article to an elevated temperature for a predetermined period of time sufficient to incorporate said antibiotic without significant modification to said fibers of said fabricated textile article such that said fiber attached antibiotic retains its characteristic antimicrobial activity.

BRIEF DESCRIPTION OF THE FIGURES

The present invention may be more easily understood and more readily appreciated when taken into conjunction with the accompanying drawing, in which.

DETAILED DESCRIPTION OF THE INVENTION

The present invention is a method for making an infection-resistance fabricated textile article which is intended for use as a biomedical appliance fashioned as a configured construct, or a therapeutic prosthesis, or a medical mechanical device. The method of manufacture described and claimed hereinafter will provide any number of different infection-resistant wound and surgical fabric dressings, infection-resistant vascular graft bypass conduits, and infection-resistant biocompatible heart valves, among many other items, for use as topical or implantable biomedical articles.

The present method of making infection-resistant textile articles provides several major advantages and desirable benefits to the commercial manufacturer and to the medical practitioner. Among these are the following:

1. The methodology is based upon structural and chemical similarities which are shown to exist between some conventionally known textile dyes and certain families of antibiotics. These antibiotics have structural features and properties, such as relative molecular mass, that are comparable or analogous to specific textile dyes; show demonstrable antimicrobial properties; are either water-miscible, or water-soluble, or water-dispersible; and are heat stable at temperatures at about and ranging from 100–300 degrees C. These features and properties allow these certain families of antibiotics to be joined as active antimicrobial agents to the fibers of textile products in a unique processing system.
2. The manufacturing methodology comprising the present invention does not utilize any liquid immersion techniques nor does the invention require submerging the fabricated textile article in any immersion baths, soaking tanks, or dipping pools for any purpose. Rather, the methodology utilizes only the technique of perfusion and structural perfusion systems in order to suffuse and infuse the antibiotic of interest into the fibers constituting the fabricated textile article.
3. The manufacturing methodology comprising the present invention also employs heat as part of the process to attach the perfused antibiotic of interest in substantially unmodified form to the fibers constituting the fabricated textile article. The attributes of the perfused antibiotic of interest permit such fiber juncture via heat treatment; and the antibiotic joined to the fibers of the fabricated textile article retains its characteristic antimicrobial activity after being subjected to such heat treatment.
4. Release of the antibiotics from the textile surface is a sustained process regulated by the properties of the particular textile material and are not controlled by exogenous binder agents.
5. Application of particular antibiotics can be made to a preformed textile device or article. There is thus no loss of antibiotic potency or concentration during fabrication of the biomedical device or article itself.

Wording, Terminology and Titles

Although many of the words, terms and titles employed herein are commonly used and conventionally understood within its traditional medical usage and scientific context, a summary description and definition is presented below for some phrases and wording as well as for particular names, designations, epithets or appellations. These descriptions and definitions are provided as an aid and guide to recognizing and appreciating the true variety and range of applications intended for inclusion within the scope of the present methodology.

To perfuse and perfusion: The action and the act of causing a liquid or other fluid to pass across the external surfaces of or to permeate through the substance of a tangible entity or configured construct. Perfusion of a liquid or fluid thus includes the alternative actions of: a sprinkling, pouring or diffusing through or over action; a covering, spreading, penetrating or saturating action (suffusion); a slow injection or other gradual introduction of fluid into a configured space or sized internal volume (infusion); and a passage across a surface or through a discrete surface or tangible thickness of matter, regardless of the mechanism or manner of transfer employed for such fluid passage.

To immerse and immersion: The action and the act of dipping, plunging or sinking a discrete entity or tangible item completely such that it is entirely submerged within a quantity of liquid or a volume of fluid. Immersion of a discrete entity or tangible item includes the alternative actions of: dunking, soaking, bathing, or flooding the entity within a liquid or fluid bath, tank, or pool; and the enveloping or burying of the tangible item in the liquid or fluid completely such that the item disappears from the surface and lies within the substance of the liquid or fluid matter.

Fabricated textile article: An article of manufacture which is comprised in whole or in part of fibers arranged to form a cloth or fabric. The fibers comprising the textile may be chosen from organic synthetics, prepared polymer compounds, or naturally-occurring matter. In addition, the textile article may alternatively be prepared as a woven cloth or as a non-woven fabric, as these are conventionally known and prepared today; and may comprise a single fiber film, or a single layer of fiber, or exist as multiple and different deniers of fibers which are present in a range of varying thickness, dimensions, and configurations.

Antibiotic: An antimicrobial agent or family of agents having a particular chemical formulation and structure which has a demonstrable set of bacteriostatic and/or bacteriocidal properties against a range of different infectious microbes, including the medically identifiable pathogenic bacteria and/or fungi of a particular order, genus and species. The range of antimicrobial properties (narrow or broad spectrum) and the manner in which such antimicrobial properties are characterized, measured, or determined is a matter of conventional knowledge and routine practice in this field.

Aqueous mixture, liquid or fluid: By definition, any mixture, liquid or fluid which contains or comprises water in any meaningful quantity or degree. Although many other compositions, substances, or materials may exist within the mixture, fluid or liquid in a variety of physical states, the bulk or majority of volume for such fluids is water.

Water-miscible substance: By definition, any composition, compound, material or matter in any physical state (i.e., gaseous, liquid or solid) that is capable of being mixed or combined with water. This term thus includes within its meaning a variety of alternative conditions and physical states for any substance which is capable of: (i) being soluble in any meaningful degree in water or an aqueous blending; (ii) being dispersible in any measurable quantity in water or an aqueous blending (whether or not a colloid is formed); (iii) being able to dissolve in any quantity in water or an aqueous blending (whether or not a homogeneous solution is formed); (iv) being able to be mixed or combined while in a simple, linear, branched, or polymerized condition or while existing in an aggregate, complex, clustered or confluent state; (v) becoming ionized or ionisable in water or an aqueous mixture; and (vi) being able to be distributed in any degree in water or an aqueous mixture while in a non-ionized state or condition.

I. The Fabricated Textile Articles

The method of the present invention is directed to the making of infection-resistant fabricated textile articles. This term "fabricated textile article" has been defined in meaning and described in scope above; and applies to any medical article, device, appliance, or construct which contains, or is constituted of, or has as a component part—in whole or in part—a fabric, cloth, or material comprised of fibers. The broad scope of this term "fabricated textile article" is intentional; and is deemed to cover and apply to any and all textile contained biomedical devices, items, entities, apparatus, appliances, and instruments which are biocompatible with and/or implantable into the body of a living subject, human or animal. Merely to illustrate some of the most common examples, a representative (but incomplete) listing of specific articles is given by Table 1 below.

TABLE 1

Illustrative Fabricated Textile Articles

Configured Fibers wound treatment dressings, films, and/or sheets
gauze pads
surgical sponges
suture material
Medical Prostheses vascular graft bypass conduits
vascular sidewall patches
vascular support bandages
catheters, catheter walls and linings, and catheter sheeting and films
Mechanical Devices heart valves and sewing rings
blood flow check valves
left ventricle assist devices
total artificial heart Fibers By definition and practical requirement, the textile of each fabricated biomedical article is composed of fibers or threads. The composition of the fibers may alternatively be: naturally-occurring matter; or be a synthetic material; or be a mixture of both of these in a wide range of varying ratios.

To illustrate the range and variety of fibers deemed suitable, Tables 2 and 3 are presented below. It will be noted that the listing of Table 2 presents both the natural fibers commonly used for apparel as well as less commonly used matter which exists in nature. In comparison, the listing of Table 3 provides representative polymeric compositions as well as other synthetic substances suitable for use in fibers. These fibers can exist in many diverse styles such as knitted, woven, braided or non-woven forms; can appear as fabric matrices of varying thickness; be fashioned as fibrous films, sheets, or cloths; and, with any or all of these forms, be combined within a single construct, assembly, or device.

TABLE 2

Naturally-Occurring Fiber Matter

Natural fibers/Protein silk;
wool;
and any mixture of these.
Natural fibers/Cellulose cotton;
flax or linen;
ramie;
hemp;
paper;
wood fibers;
and any mixture of these.

TABLE 3

Illustrative Synthetic Fiber Materials

Polymeric Fibers polyethylene terephthalate;
nylon;
polyurethane;
polyglycolic acid;
polyamides;
and mixtures of these substances.
Other synthetic fiber materials acetate;
triacetate;
acrylic;
acrylonitile;
aramid;
modacrylic;
olefins;
propylene;
ethylene;
polytetrafluoroethylene;
polyesters;
saran.

At least some of the fibers comprising the textile portion of the fabricated biomedical article (regardless of whether composed of naturally-occurring matter, synthetic materials, or a mixture of these), will demonstrate certain properties and characteristics.

1. The fibers will have a demonstrable capacity to take up water and/or aqueous liquids and fluids (with or without direct wetting of the fiber material). The mode or mechanism of action by which water and aqueous fluids is taken up by the fibers of the textile (and/or become wetted by the aqueous fluid) is technically insignificant and functionally meaningless. Thus, among the different possibilities of water uptake are the alternatives of: absorption; adsorption; cohesion; adhesion; covalent bonding; non-covalent bonding; hydrogen bonding; miscible envelopment; water molecule entrapment; solution-uptake between fibers; fiber wetting; as well as others well documented in the scientific literature. Any and/or all of these may contribute to water or aqueous fluid uptake in whole or in part. Which mechanism of action among these is actively in effect is irrelevant.

2. By choosing the particular chemical formulation and/or stereoscopic structure for the fiber substance, the fibers as a whole and the resulting textile may be prepared as articles having relatively short or meaningfully long duration and lifespan for functional use. Thus, by choosing one or more synthetic polymers having recognized water-erosion and biodegradation properties, the textile can be manufactured as a biodegradable fabric with an expected useful lifespan of only days or weeks. Alternatively, by choosing only durable and highly resilient matter as fibers, fabricated textiles of many years duration and medical utility may be routinely made. All of these choices, variables, and alternatives are conventionally known practices commonly available and used by practitioners in this field.

3. The fibers comprising the textile of the biomedical article can be utilized in a variety of structures to form a framework or organizational structure. Thus, as conventionally recognized within the textile industry, the fabric may alternatively be a woven or non-woven construction; may exist either as a single layer fabric or be prepared in multiple layer construct form where each layer may vary in denier size or thickness; and may receive one or more surface treatments, protein coatings, or chemical overlays to import or enhance desired attributes such as in-vivo biocompatibility, a scoured external surface, or greater resiliency over time. All of these organizational variances and constructional alternatives are routine matters which will be chosen as a matter of particular needs or personal choices.

4. The fibers comprising the textile in the fabricated medical article can be prepared to meet the particular intended use circumstances or contingencies of the particular application. Thus, the constructed fabric can alternatively be prepared as a felt material; or as a thin gauze; or as a thick-walled configured tube; or as a cloth film lining the exterior or interior of a mechanical medical appliance or prosthesis. Equally important, the fibers and resulting textile construct may take form as a stiff, inflexible or unyielding cloth wall; or as a thin, very flexible, geometrically configured fabric segment; or even as a cord or string-like length of material.

II. The Structural And Chemical Similarities Between Some Textile Dyes And Certain Antibiotics Dyes (organic compounds that are colored) must possess certain properties for binding such as demonstrable solubility during application; a degree of fibrophilicity; and fastness for selective fibers. The number of chemical structures that possess such properties is extensive, with several thousand dyes commercialized. Most dyes are based on azo- and anthraquinone chemistry, although many other chemical types have been used. A majority of these dyes have relative molecular masses (r.m.m.) in the 300–1,500 range and depending on the fiber to which they are applied, can be anionic (usually via sulfonic or carboxylic acid groups), cationic (quaternized nitrogen) or nonionic with slight solubility derived from hydrophilic hydroxy or amino groups. Beyond the r.m.m. and functionality of the selected dye, it is difficult to predict the extent or strength of interaction between dye and fiber based solely on molecular structure. Disperse dyes, a class of dyes that have a strong affinity for polyester, are of particular interest and represent the type of interaction that would be a model for assessing antibiotic adhesion to the surface.

Similar to dyes, there are many types of compounds that have antimicrobial activity. Antibiotics have numerous functions, from prevention of bacterial wall formation to inhibition of DNA function and protein synthesis. Their mode of action is directly dependent on their detailed chemical structure, which can vary widely between different classes of antibiotics but can vary slightly within the same class. These variations in structure distinguish the various families of antibiotics, spectrum of activity, side effects, and clinical usefulness. Many antibiotics have structural features (solubility, r.m.m., anionic or H-bond forming functional groups) that are comparable with those of dyes, as shown by Table 4 below.

TABLE 4*

| DYES | ANTIBIOTICS |
|---|---|
|  A |  A⁰ |
|  B |  B' |

TABLE 4*-continued

| DYES | ANTIBIOTICS |
|---|---|
|  |  |
| C | C' |

*Reproduced from: Phaneuf et al., "Merging Of Biomedical and Textile Technologies in Order to Create Infection Resistant Prosthetic Vascular Grafts," in Antimicrobial/Anti-Infective Materials (Sawan, S. P. and G. Manivannan, editors), Technomic Publishing Co., Inc., Chap. 10, pp. 239–259 (2000).

The Fluoroquinolone Antibiotics

In order to utilize an antibiotic using dyeing conditions, the antibiotic structure would have to have a relative molecular mass (r.m.m.) in the 300–1,500 range as well as be heat stable. A "compact" chemical structure, based on aromatic rings of disperse dyes, would also be a requirement. The exemplary fluoroquinolones, as shown in Table 1, are of particular interest. This family of antibiotics now extends to at least twelve members (Ciprofloxacin, Ofloxacin, Norfloxacin, Sparfloxacin, Tomafloxacin, Enofloxacin, Lovafloxacin, Lomefloxacin, Pefloxacin, Fleroxacin, Avefloxin, and DU6859a); and has become the drug of choice for many applications. These antibiotics are effective at low concentrations; and hold an ideal antimicrobial spectrum against microorganisms most commonly encountered clinically in vascular graft infection, with significant activity against relevant pathogens such as *S. aureus*, methicillin-resistant *S. aureus*, *S. epidermidis*, Pseudomonas species, and *Escherichia coli*. Fluoroquinolones are heat stable; are of 300–400 r.m.m.; and have many structural features analogous to dyes. Thus, these antibiotics possess characteristics desirable for textile dyeing.

III. The Manner Of Interaction Between Textile Fibers And Small Dye Molecules In non-biological systems, the forces of attraction between simple structural molecules and polymers as well as the resulting diffusion have been studied most extensively for fibers and dyes. Literature on dye-fiber interactions is extensive and has been well summarized (see for example: Nunn, D. A., *The Dyeing of Synthetic Polymers and Acetate Fibers*, Dyers Publication Trust, Bradford, U. K., 1979; Johnson, A., *Theory of Coloration of Textiles*, Society of Dyers and Colorists, Bradford, U. K., 1989; Shore, J., *Colorants and Auxiliaries*, Society of Dyers and Colorists, Bradford, U. K., 1990).

The study of dye-fiber interactions is founded on physical chemistry; and is divided into thermodynamic and kinetic properties. Kinetic studies characterize the rate at which dyes diffuse into and from fibers. Thermodynamic studies of the equilibrium state describe the forces of attraction, in both quantitative and qualitative terms. Changes in affinity, altering with variation in the structural features of dyes, have been widely studied and are typically used to explain the observed phenomena. Many studies have been conducted in these areas, each covering a series or family of dyes having closely related structures. While many experimentally observed interactions can be adequately explained, it has proven difficult, if not impossible, to predict these interactions accurately from the structural data alone.

It is therefore both useful and beneficial here to review briefly some details concerning the kinetic properties and the thermodynamic properties of conventionally known small dye molecules. This information is presented as a guide in order that the uncertainties of dyeing processes and procedures be properly recognized and appreciated.

Kinetic Properties

The diffusion of dyes into fibers requires "access" and depends on the swelling of the fiber in the application medium (usually aqueous) and/or the segmental mobility of the polymer chains at the application temperature. Two of the critical polymer parameters are:

(1) the swelling in water, for which a convenient guide is the standard moisture regain; and
(2) the second order glass transition temperature, $T_g$. In hydrophobic polymers (such as polyester), the $T_g$ of the polymer is a key factor; since little swelling takes place, the dye occupies a free volume space within amorphous areas of the polymer and dye diffusion takes place via segmental jumps of polymer chains. In comparison, with water-swollen polymers, swelling is a better measure of accessibility' with dye diffusion proceeding through water-filled pores within the polymer. The relative merits of the "pore model" versus the "free-volume model" have been discussed and reviewed; and, for intermediate cases of moderate swelling, some combined models have been suggested [Hori et al., *J. Soc. Dyers Color*. 97: 6 (1981)]. Such studies of dye diffusion within textile fibers are based on Fick's laws of diffusion; and their application inevitably involves some assumptions—such as the homogeneity of polymer morphology and circularity of fiber cross section. Nonetheless, comparative values of diffusion coefficients can be obtained which serve as useful measures of the molecular diffusion rate for a given fiber.

Thermodynamic Properties

Dye diffusion into fibers also requires various forces to achieve a transfer greater than that of simple imbibition. There are several potential factors for this phenomenon, with the relative contribution varying from fiber to fiber and from dye to dye. These are divided into the following categories:

1. Ionic interactions: These occur between cationic charges generated by protonation of amino groups in silk and nylon and anionic moieties (sulfonic acid and carboxylic acid) of dyes. The pH of application is chosen to achieve the appropriate level of attraction. Using the interactions, fluoroquinolones (which contain carboxylic acid groups) are believed to interact with fibers such as nylon and silk.
2. Polar interactions: These have numerous classifications including dipole-dipole, dipole-induced dipole and hydrogen bonds. Functional groups capable of involvement in such interactions such as amine and hydroxy groups are widespread in fibers as well as in dyes. Fluoroquinolone antibiotics also contain these groups and are expected to interact in this way.

3. Non-polar interactions: These are referred to as London forces, dispersion forces, or non-polar Van der Waal's forces; and may contribute to the overall driving force from a dissociation of the solute dye for the aqueous environment. The types of hydrophobic interactions are also implicated in the ability of dye molecules to aggregate, thus playing an important role to the overall attraction these aggregates to the fiber. The effects of dispersion forces are not only proportional to the r.m.m. but also rely on close proximity between the interacting molecules. Therefore, differences in molecular configuration are important.

These different types of interactions and binding forces not only control the dye removal from the solvent bath or exhaustion onto the fiber during application, but may also play a large part in determining the fastness of the dye in use, since these forces are reversible. Additional dye fastness can be achieved via covalent bonding or by chemical modification of the dye into a less soluble form. Where there are no such additional considerations, subsequent resistance to wet treatments can be very limited, resulting in dye desorption or leaching out of the dye from the fabric. For any chosen dye, this effect represents a limit to achieving satisfactory performance. However, a controlled and sustained leaching of a "dyed" antibiotic would represent a major contribution of value to infection resistance for a textile in medical applications. Thus, an understanding of both the forces that bring together dyes and fibers and the rate at which the dye diffuses within the polymeric substrate will be of critical importance in the study of antibiotic-fiber interactions.

IV. The Benefit And Value Of The Perfusion Technique

The perfusion technique and use of pad/heat processing (thermofixation or wet-heat application) has many advantages over current antimicrobial applications. One of the main advantages is that no exogenous binder agents are required to maintain antibiotic release and long-term infection resistance. This perfusion technique also has benefits in that the antibiotic of choice can be applied to preformed devices and existing articles of manufacture. Therefore, antibiotic release would not occur during the manufacturing process. Moreover, this technology is not a dipped process in which, without the addition of heat, no infection resistance can be generated or maintained.

Perfusion of the textile material permits penetration of the antibiotic of choice throughout the matrices of the textile. The perfusion process thus provides complete wettability (and wetting)—in contrast to dipping which relies on only the wicking properties of the particular textile. Such complete wetting of the surface provides antibiotic incorporation both into and through the textile material.

Perfusion Versus Dipping Methodology

The perfusion technique has several advantages over the prior art process of dipping in that: (1) the textile fabric is exposed to a constant concentration over the perfusion time; (2) the application of antibiotic is leveled throughout the entire fabric matrices, that is to say that antibiotic application is uniform across the fabric; and (3) antibiotic is perfused/applied throughout various device configurations and designs. Thus, the perfusion of an antibiotic across a textile fabric in conjunction with pad/heat dyeing is a technique which results in a uniformly treated material with antimicrobial activity.

An illustrative recitation and representative example of the present invention is the preferred manner and mode for practicing the methodology as set forth below. It will be expressly understood, however, that the steps and manipulations outlined below are subject to variances and changes in the procedural details—all of which are deemed to be routine and conventional in this field and may be altered at will to accommodate the needs or conveniences of the practitioner.

Illustrative Technical Description of Antibiotic Perfusion and Pad/Heat Dyeing A textile article [fabric, layer, sheet or film as described in the wording, terminology and titles section herein] is employed. This textile article can be comprised of either polyester, nylon, silk or cotton (as representative examples); and can be used typically in a cylindrical or flat sheet format. For perfusion of a cylindrical fabric, a 15 cm segment of the material is secured to a porous polyethylene mandrel using 2-0 silk. For perfusion of a flat fabric segment, a porous polyethylene sheet (4 cm×4 cm) is used and tied at the edges with 2-0 silk. Both of these holders can be varied in dimensions (length and width) to accommodate a range of variously sized textile fabrics.

The respective textile fabric is then placed into a polyethylene flow chamber and secured via a pressure fitting in conjunction with Teflon tape. For the flat sheet, the two chambers are connected using screws. In the cylindrical chamber, a polyethylene cover containing an opening is placed over the top of the chamber to secure the outlet fitting. Inert Tygon tubing (¼" I.D.) is fit over the upper connector followed by attachment to a Y-fitting. All tubing is connected using adjustable clamps.

One part of the Y-fitting is then connected to a Harvard Apparatus Peristaltic Pump and continued onto the inlet connector on this chamber. Tygon tubing is connected to the other part of the Y-fitting and the other end placed into a reservoir containing an antibiotic solution, for example, Cipro. Other fluoroquinolone antibiotics or antibiotics containing an aromatic moiety [such as a benzene ring] within the structure can also be employed.

An antibiotic concentration of 5 mg/ml (total volume 200 ml) is preferably utilized. However, a variety of antibiotic concentrations ranging from 1–400 mg/ml typically can be used. Also, the total volume of antibiotic solution can be increased as needed to compensate for a larger perfusion chamber.

The configured textile fabrics are preferably perfused at a rate of 12 ml/minute for about 1 hour. Perfusion rates ranging from 1–100 ml/minute and perfusion times ranging from about 30 minutes to more than 24 hours can be employed based on parameters such as the material thickness, hydrophobicity, and the like. After perfusion is completed, all textile materials are removed and dried (preferably air-dried) for 24 hours. If desired, low dry heat (50° C.) can also be used to decrease drying times.

Antibiotic uptake and fixation into the textile can then be performed using either of two processing techniques. The textile material is preferably placed onto a metal hanger. The first processing technique is thermofixation; and comprises hanging the textile and applying intense dry heat to the textile (typically 210° C.) for a specific time (typically 2 minutes).

However, a variety of different dry heat temperatures ranging from about 100 to 300° C. and differing heating times ranging from less than 15 seconds to about I hour can be employed.

In comparison, the second fixation technique uses solution-dyeing in order to incorporate and fix the antibiotic into the textile fabric via a wet-heat application process. The perfused textile provides a leveled concentration of antibiotic across the thickness of the textile. The perfused textile is therefore placed (immersed) into a comparable antibiotic concentration dye bath (e.g., 5 mg/ml) and heated while immersed to elevated temperatures ranging from about 60–120° C. for a variety of time durations ranging from about 10 minutes to about 24 hours. Performance and completion of either of these two antibiotic fixation procedures subsequent to perfusion of the configured textile results in significant incorporation and fixation of antibiotic in the configured textile fabric, thereby creating an infection-resistant material.

V. Experiments And Empirical Data

The following experimental and test data are presented as both proof of principle and as the best examples of the present invention. By its very nature, therefore, the various experiments described and the empirical results observed merely illustrate the scope of the present invention and serve as representative examples of the unique process.

Experimental Series A*[1]

[1] Substantively reproduced from: Phaneuf et al., "Merging Of Biomedical and Textile Technologies in Order to Create Infection Resistant Prosthetic Vascular Grafts," in *Antimicrobial/Anti-Infective Materials* (Sawan, S. P. and G. Manivannan, editors), Technomic Publishing Co., Inc.), Chapter 10, pp. 239–259, 1999.

Application of Fluoroquinolones to Polyester via Liquid Bath Saturation Followed by Pad/heat Dyeing Pad/Heat Dyeing of Liquid Bath Applied Ciprofloxacin (Cipro) and Ofloxacin (Oflox)

A textile dyeing technique known as thermofixation or pad/heat was employed to "dye" Cipro and Oflox to woven polyester after the polyester was first saturated with the antibiotic in a liquid bath. Pad/heat dyeing focuses on two main principles: the fibrophilic characteristics of the "dye" molecule; and intense, dry heat. This pad/heat dyeing technique has several advantages over previous antibiotic binding methodologies such as liquid bath saturation alone: (1) Cipro and Oflox would be attached directly to the fibers without molecular modification thereby maintaining full antimicrobial activity; (2) higher antibiotic concentrations can be applied since binding sites are not required; (3) leaching effects should be controlled and sustained due to the potential affinity of the Cipro/Oflox structure for polyester and (4) use of external ligands or cross linkers is eliminated, avoiding concerns over drug carrier toxicity, biocompatibility, and mutagenicity. Polyester "dipped" or immersed into a liquid bath of the respective antibiotic but not heat treated was selected as the control, a feature which was notably absent in a majority of the previous studies evaluating infection-resistant materials.

Experiment 1: Determination of Cipro/Oflox Heat Stability

An inoculum of *S. aureus* was diluted to obtain a bacterial concentration of $10^6$ *S. aureus*/ml. Maximum inhibitory concentration (MIC) and maximum bacteriocidal concentration (MBC) for Cipro and Oflox, both native and heated to 135° C. for 1 hour (dye bath conditions) were determined utilizing standard microbiological techniques [Finegold, S. M. and E. J. Baron, *Diagnostic Microbiology*, 7$^{th}$ ed., C. V. Mosby, St. Louis, 1986]. Antibiotic concentrations in the assay were 0.19, 0.39, 0.78, 1.56, 3.13, 6.25, and 1.25 ug/ml. Qualitative examination of the Trypticase Soy Broth (TSB) solutions to determine the MIC was performed by observation of bacterial growth (as indicated by turbidity) after 24 hours. The broth solutions were then backplated on agar plates and examined after 24 hours to determine the MBC. Both native and heat treated Cipro had a MIC of 2.3 uM (n=6), and a MBC of 6.5 uM (n=6), comparable to native and heat-treated Oflox MIC (0.78 uM; n=6) and MBC (9.5 uM; n=6). Thus, the antimicrobial activity of both Cipro and Oflox was retained after exposure to standard dye bath conditions.

Experiment 2: Pad/Heat Application of Cipro/Oflox onto Polyester

Polyester segments (1 cm) were immersed and saturated in a bath with 200 ul of either a Cipro or Oflox solution (5 mg/ml) and air dried. The bath dipped/immersed segments were then placed into a 210° C. oven for 2 minutes in order to increase quinolone penetration into the fiber. Quinolone-associated fluorescence in the cross-sections of polyester fibers confirmed antibiotic presence within the fibers (data not shown). By measuring the absorbance of the antibiotic applied and released from polyester, the total amount of Cipro bound via pad/heat to each segment was calculated to be 33 ug/cm2±3.0 (n=12) whereas the Oflox pad/heat segment had 16 ug/cm2±4.2 (n=5) bound. The difference in antibiotic uptake is hypothesized to be the result of variation in molecular structure between the two antibiotics.

Experiment 3: Determination of Antimicrobial Properties for Pad/Heat Treated Polyester Segments Oflox and Cipro pad/heat treated samples (prepared as described above) were also tested against various *S. aureus* concentrations. The stock inoculum was diluted to $10^7$, $10^6$, $10^5$ and $10^4$ bacteria/ml. After sterilization, treated polyester segments were placed in 2 ml of the bacteria solutions for 24 hours at 37° C. and the broth solutions were backplated. Treated samples were transferred to sterile 50 ml polypropylene tubes containing 30 ml of sterile phosphate-buffered saline solution (PBS). Sonication of samples was achieved at 60 Hz for 10 minutes in an ice bath. After 10 minutes, 100 ul of the sonicate solution was backplated onto an agar plate. Colony forming units (CFUs) were counted on the backplates after 24 hours to determine the presence of adherent bacteria on the starting samples. From backplate and sonicate data, the maximum inhibitory and bacteriocidal properties of treated 1 cm$^2$ segments were determined. Overall, both Cipro and Oflox treated polyester segments demonstrated antimicrobial activity against a sizable inoculum: inhibiting the growth of $10^7$ organisms and killing $10^6$.

Experiment 4: Spectrophotometric Analysis of Cipro Release

All liquid bath control and pad/heat segments were washed for 10 minutes in PBS prior to testing to remove any loosely bound antibiotic remaining from the bath liquid. To assess release pharmacokinetics, treated polyester segments were placed into 5 ml of PBS at 37° C. These segments were incubated in a 37° C. water bath and sampled at 10 minutes, 24, 48, 72, and 96 hours. Fresh PBS (5 ml) was replaced after each sampling. The antibiotic concentration in the wash bath fluid was determined spectrophotometrically, with the percent Cipro and Oflox released determined. The results of the analysis are graphically shown by FIG. 1.

Figure 1:
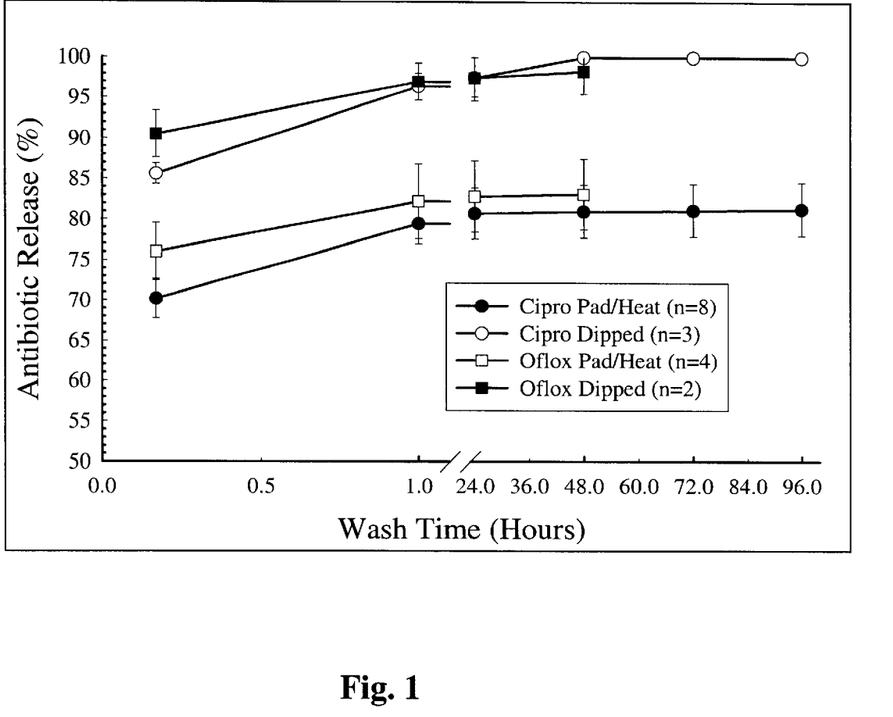
FIG. 1 is a graph presenting the release rates for the antibiotics Ciprofloxacin and Ofloxacin as a function of wash time in a 37° C. water bath.

As illustrated by the graph of FIG. 1, Cipro was completely released from the segments within 48 hours of washing, in contrast to the Oflox dipped segments which released a majority of the antibiotic between 1 and 24 hours. Cipro pad/heat segments lost 69% of the antibiotic immediately followed by a slow, sustained release over 96 hours. In contrast, Oflox treated segments lost 76% of the antibiotic followed by minimal release over the remaining 48 hours. Although Oflox release was not significantly sustained, the antibiotic was still present within the polyester segments as determined by fluorescence.

Experiment 5: Zone of Inhibition Assay

Control and pad/heat treated segments from the washing model (Experiment 4 above) were also examined for antibiotic release using a zone of inhibition assay. Polyester segments (1 cm ) were washed for various time periods, sterilized, and then plated on agar streaked with *S. aureus*. The zone of inhibition was then measured after overnight incubation. The inhibition results are graphically shown by FIG. 2.

Figure 2:
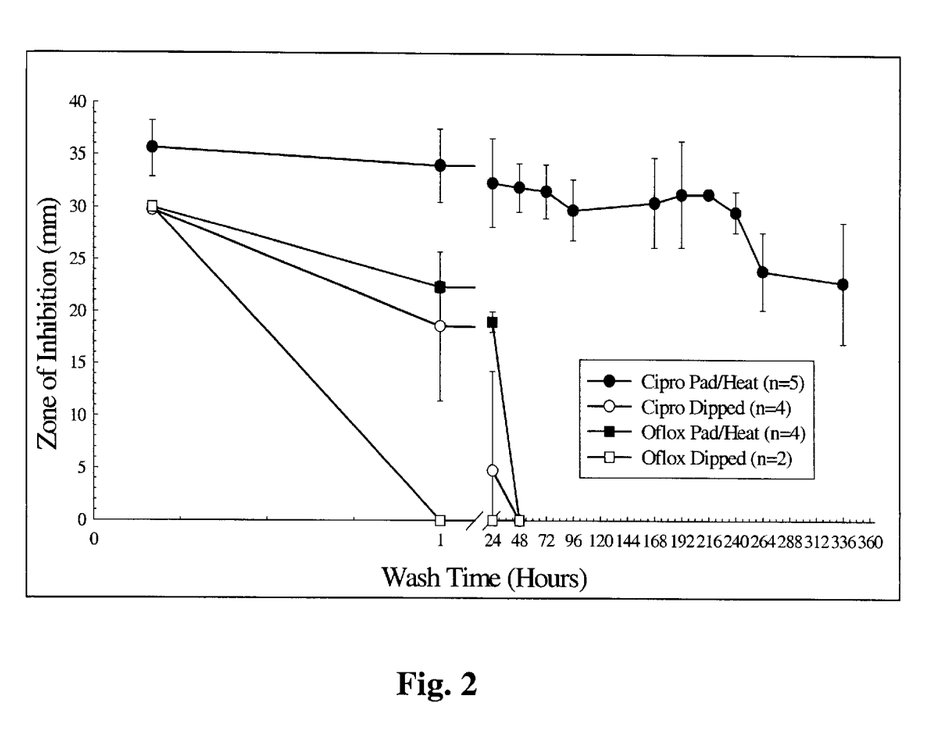
FIG. 2 is a graph presenting the zone of inhibition against *S. aureus* by differently prepared textile segments containing the antibiotics Ciprofloxacin and Ofloxacin.

As seen in the graph of FIG. 2, the Cipro dipped segments did not have any antimicrobial activity within 48 hours whereas the Oflox dipped segments did not possess antimicrobial activity within 1 hour of washing. Cipro pad/heat treated polyester continued to demonstrate anti-staphylococcal activity past 336 hours and were further evaluated in vivo. However, the Oflox treated segments lost antimicrobial activity within 48 hours. Interestingly, all of the early zone of inhibition findings (<96 hours) correlated with the data generated via the spectrophotometric assay, establishing the spectrophotometric assay as an accurate indicator of antibiotic release pharmacokinetics from the graft surface.

Experiment 6: In Vivo Results

The Cipro pad/heat treated polyester was then evaluated for antimicrobial activity in an in vivo model. One $cm^2$ polyester segment (either plain, Cipro dipped, or Cipro pad/heat treated) was implanted in the dorsal subcutaneous tissue of rabbits and directly contaminated with $10^6$ *S. aureus*. After one week, the samples were sterily harvested. Wounds were blindly graded on a scale from 1 (no evidence of infection, good tissue incorporation) to 4 (suppurative infection extending outside of the graft pocket, no gross tissue incorporation).

Figure 3:
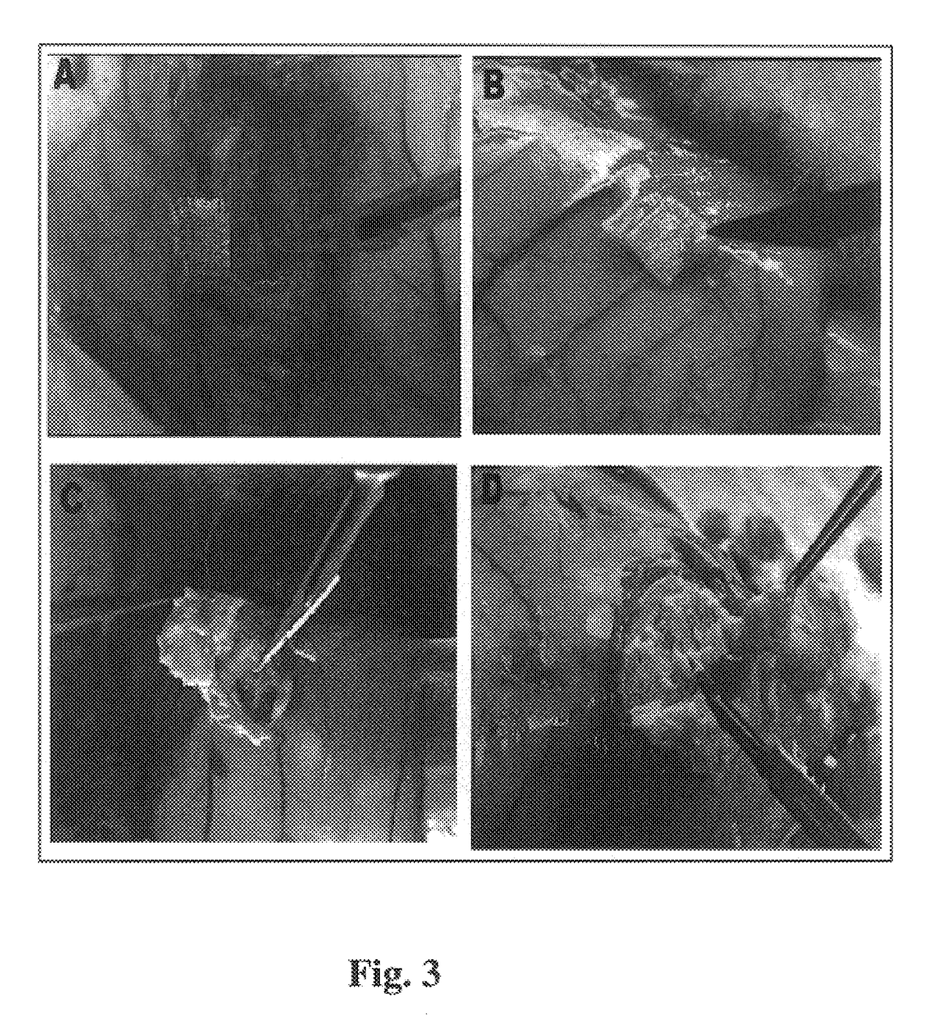
FIGS. 3A–3D are photographs illustrating the grading system utilized to evaluate gross wound appearance after in-vivo implantation.

FIG. 3 as a whole is an illustration representing the grading system utilized to evaluate gross wound appearance. A grade 1 wound, as shown by FIG. 3A, showed no evidence of infection with good tissue incorporation, the primary category of Cipro pad/heat treated segments. A grade 2 wound, as shown by FIG. 3B, is representative of the Cipro-dipped segments, had minimal purulence involved with a portion of the segment as well as partial tissue incorporation. A grade 3 wound, as shown by FIG. 3C, had infection throughout the pocket with no tissue incorporation, and a grade 4 wound, as shown by FIG. 3D, had infection extending outside the pocket, also with no tissue incorporation. The untreated polyester segments were primarily in these categories.

Experimentally also, hematoxylin and Eosin sections were performed to characterize the microscopic interactions (e.g., inflammatory response) as well as macroscopic tissue incorporation (e.g., macrophages, fibroblasts, protein) between untreated, dipped and pad/heat treated polyester. Gram staining was also performed to determine the presence of coagulase negative microorganisms. The results are graphically shown by FIG. 4.

Figure 4:
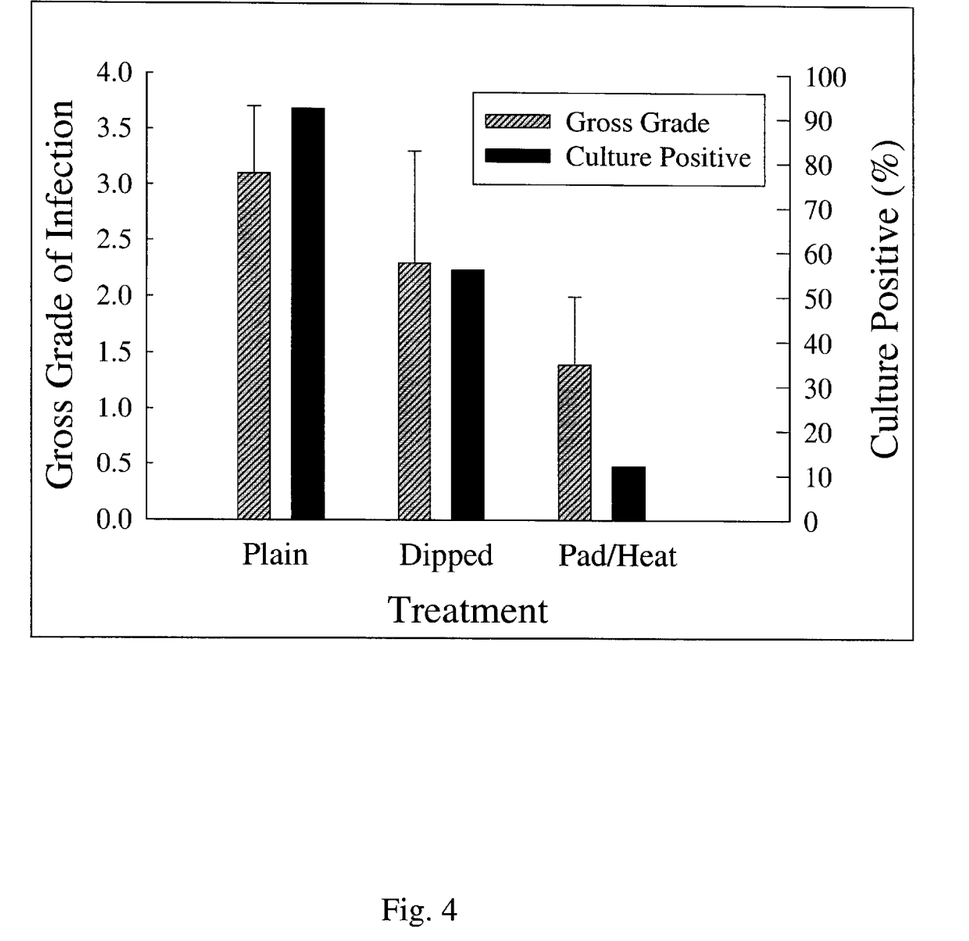
FIG. 4 is a graph presenting the gross infection grade and percent culture-positive infection results for differently prepared textile segments containing Ciprofloxacin.

As seen in the graph of FIG. 4, the data presents details concerning gross infection grade (lined bars) for untreated, Cipro-dipped, and pad/heat-treated polyester. Pad/heat-treated segments had a significantly lower wound grade as compared to dipped (p<0.05) and untreated (p<0.001) segments. Also, there was a 4.7 and 7.6-fold decrease in percent culture-positive segments as compared to these segments, respectively.

Moreover, the data of FIG. 4 shows that untreated polyester was easily infected in this model (mean grade 3.1±0.6). Notably, however, a significant (p<0.05) wound grade difference between the Cipro dipped (2.3±1.0) and pad/heat (1.4±0.6) samples was demonstrated. Determination of adherent bacteria present on the implanted polyester segments via sonication and culture studies again revealed a 4.7-fold difference between the dipper (56% culture positive) and pad/heat (12% culture positive) groups. The dipped and pad/heat segments had 1.6 and 7.6-fold less positive cultures as compared to untreated polyester (92% culture positive).

Histologic studies also correlated with the gross grade observations. This is illustrated by FIGS. 5A–5D, respectively.

Figure 5:
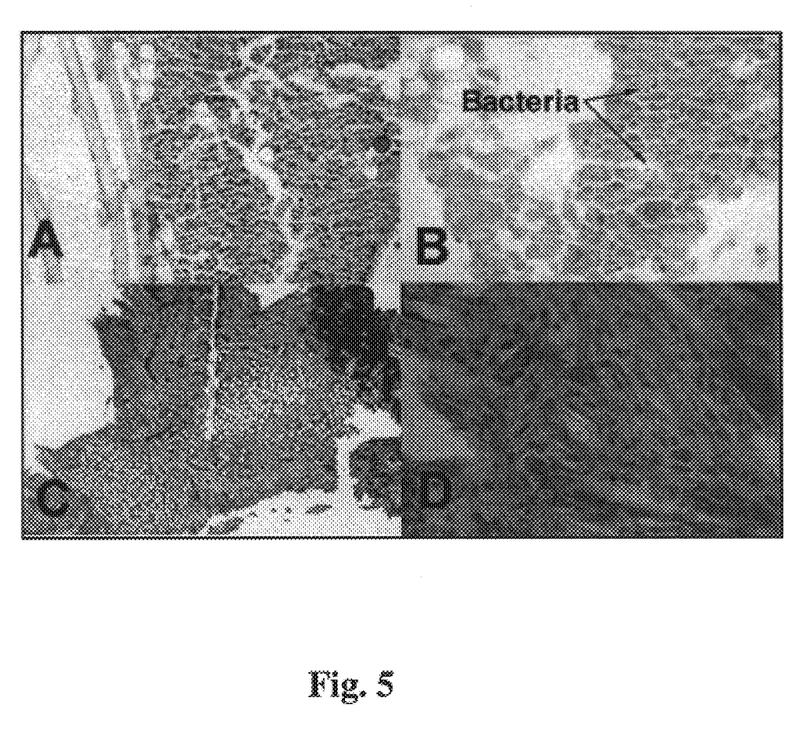
FIGS. 5A–5D are microphotographs of histological studies correlated with the gross grade observations for differently prepared textile segments containing Ciprofloxacin.

As revealed by the photographs of FIG. 5, the histologic evaluation of untreated and Cipro pad/heat-treated polyester is shown. Untreated polyester, stained with hematoxylin and eosin, showed poorly incorporated fibers with extensive polymorphonuclear infiltrate, Russell bodies, and necrosis. FIG. 5A shows the gram staining of these segments identified gram-positive cocci (asterisk) within the inflammatory infiltrate. In contrast, FIG. 5B shows pad/heat-treated polyester showed good tissue incorporation with engulfment of the fibers by tissue macrophages and essentially no acute inflammatory response. FIG. 5C shows there was also no evidence of necrosis or infection. Finally, under high-power magnification, FIG. 5D shows tissue incorporation and healing are evidenced by tissue macrophage and fibroblastic encasement. No inflammatory elements are seen.

Overall therefore, untreated polyester had micro and macro abscess formation with intense polymorphonuclear (PMN) reaction and surrounding tissue necrosis. No tissue ingrowth was evident; and using gram staining, numerous coagulase negative organisms were present. The dipped segments also exhibited these characteristics, but were less intense. Minimal tissue incorporation was also visible. In contrast, the pad/heat specimens showed good tissue incorporation with minimal to no gram positive organisms.

Conclusions

1. Pad/heat dyeing after immersion and saturation in a liquid antibiotic bath is a rapid and effective methodology for applying dyes as well as antibiotics to various materials under conditions in which the dye moiety has limited fibrophilicity in conjunction with greater affinity for the dye bath. An important criteria for dyeing is dye stability to the application conditions. Cipro and Oflox, when applied via a saturating liquid bath and exposed heating conditions utilized in pad/heat dyeing, possessed excellent structural stability as determined by no variation in antimicrobial activity (i.e., MIC/MBC); and no structural degradation upon dye bath analysis via HPLC (data not shown). In preliminary studies, the conventional dye bath saturation technique was used alone initially in an attempt to apply both antibiotics to polyester. Due to limited fibrophilicity and greater hydrophilicity, minimal antibiotic was dyed onto the polyester as determined by no reduction in dye bath absorbance. In contrast, antibiotic bath saturation followed by pad/heat dyeing bound significant amounts of both Cipro and Oflox onto the textile segments. Cipro dyeing onto polyester was two fold greater than Oflox, potentially due to greater degree of fibrophilicity inherent in the Cipro structure.

2. Based on dye theory, both antibiotics bound to polyester using pad/heat were limited to the outer periphery of the fiber and not throughout the fiber as displayed by the slow, sustained antibiotic leeching. This minimal penetration by Cipro and Oflox is caused by the relatively low degree of fibrophilicity of the antibiotic as compared to standard polyester dyes. Conversely, dipping polyester into liquid baths containing equivalent concentrations of the antibiotic but without heating resulted in non-specific binding as confirmed by rapid release of the antibiotic within 24 to 48 hours.

Experimental Series B:

Application Of Oflox To Silk And Nylon Via Liquid Bath Saturation Followed By Pad/Heat Dyeing Pad/Heat and Aqueous Dyeing of Oflox onto Silk and Nylon For preparing pad/heat samples, one segment of both silk and nylon (36 cm$^2$—4 segments/material) were simultaneously dipped into a saturating bath of 5 mg/ml Oflox solution (10 ml total volume), air-dried and then placed into a 210° C. oven for 2 minutes in order to increase quinolone penetration into the fiber. In comparison, silk and nylon aqueous dyeing was performed by simultaneously exposing the segments to a liquid bath containing 10 ml of a 5 mg/ml (10 ml) Oflox solution at 80° C. for 1 hour. The samples were then air-dried. Quinolone-associated fluorescence in the cross-sections of polyester fibers confirmed antibiotic presence within the fibers (data not shown). The controls for pad/heat prepared and aqueous dyeing samples were silk and nylon segments simultaneously dipped into a liquid bath containing 5 mg/ml Oflox solution for 1 hour followed by air-drying.

Zone of Inhibition Assay

Control and pad/heat or aqueous dyed treated segments were examined for initial antibiotic release using a zone of inhibition assay. Segments (1 cm$^2$) were washed for either 30 minutes or 24 hours, sterilized and plated on agar streaked with *S. aureus*. The zone of inhibition was then measured after an overnight incubation. Oflox dipped silk segments had a zone of inhibition for both treatments after 24 hours of washing (22.3±0.6 cm and 11.6±0.6 cm). In contrast, Oflox dipped nylon segments had no antimicrobial activity after 24 hours. Oflox dyed and pad/heat treated silk both had zones greater than the respective dipped segments (27.6±0.6 cm and 19±1.1 cm). Nylon dyed segments, similar to controls, had no antimicrobial activity after 24 hours. However, the pad/heat treated samples had a zone of inhibition at 24 hours (18.6±0.6 cm), demonstrating the specificity of the application method with the material.

Experimental Series C:

Application Of Cipro To Knitted Dacron Vascular Graft Material Via A Luminal Perfusion System Graft Preparation Knitted Dacron double velour vascular grafts (100 cm length) were scoured in a 1 L Tween 20/sodium carbonate solution at 60° C. for 30 minutes followed by a distilled water wash at 60° C. for 30 minutes. The grafts were then hydrolyzed by exposing the textile to 1% sodium hydroxide at 100° C. for 30 minutes. This procedure permits increased wetability of the Dacron fiber. The grafts were rinsed with distilled water and dried at 80° C. for 1 hour. Both scoured and hydrolyzed segments (15 cm) were cut and used for each perfusion.

Inward Infusion Luminal Perfusion System

Figure 6:
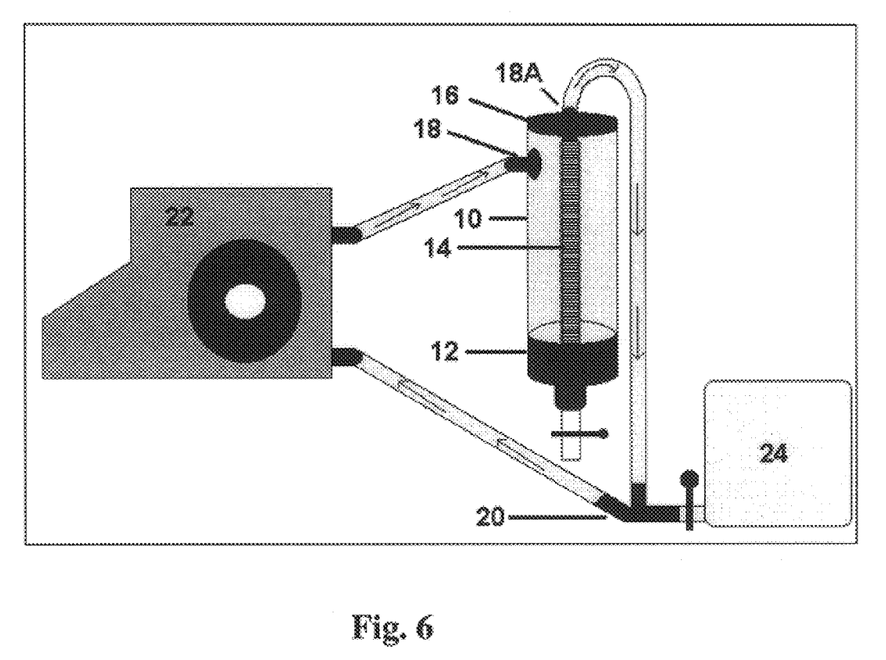
FIG. 6 is an illustration of a structural perfusion system suitable for perfusing a prepared aqueous antibiotic fluid across a vascular graft tubular segment formed of scoured Dacron fiber.

A proprietary perfusion system was developed in order to incorporate antibiotic throughout the fibers of the graft as shown by FIG. 6. As FIG. 6 illustrates, a 60 ml polyethylene chamber was designed for infusion with inflow and outflow fixtures in order to circulate an antibiotic liquid throughout the system. A porous, hollow inner polyethylene mandrel (12) attached to 6 mm tubing connectors (18) was prepared. A scoured and hydrolyzed graft segment (14) was connected to this fitting via 2-0 silk and inserted into the flow chamber (10) through a pre-fit seal secured with Teflon tape. A cover (16) was placed over the top of the chamber (16) in order to stabilize the upper connector. Inert Tygon tubing (¼" I.D.) was fit over the upper (withdrawal) connector, followed by attachment to a Y-fitting (20). One part of the Y-fitting was connected to a Harvard Apparatus peristalic pump (22) that continued onto the side connector (inlet feed) of the chamber, thereby completing the perfusion loop. Tygon tubing was connected to the other part of the Y-fitting, which was inserted into a reservoir (24) of Cipro solution (5 mg/ml).

Any antibiotic at various concentrations can be housed in this system for infusion/perfusion of the textile. The flow rate was about 12 ml/min and the system was run for 1 hour. After perfusion, the graft was removed from the chamber with one connector remaining attached and air-dried. Infection-resistant properties for the scoured Dacron are the result. Antimicrobial activity of hydrolyzed grafts is deemed to increase owing to the better wetting properties of the material.

The present invention is not to be restricted in form nor limited in scope except by the claims appended hereto.

We claim:

1. A method for making an infection-resistant fabricated textile article useful for biomedical applications in-vivo, said method comprising the steps of:

obtaining a fabricated textile article comprised of at least one type of fiber matrices able to take up aqueous fluids;

preparing at least a minimum inhibitory concentration of an aqueous antibiotic fluid consisting of water and at least one water-miscible antibiotic composition which has recognized antimicrobial properties, is heat stable and has a relative molecular mass in the 300–1500 range;

perfusing said prepared antibiotic fluid across said fiber matrices of said fabricated textile article for a sufficient period of time such that said aqueous antibiotic fluid permeates at least some of said fiber matrices comprising said fabricated textile article;

allowing said antibiotic perfused fabricated textile article to dry; and heating said dried antibiotic perfused fabricated textile article to an elevated temperature for a period of time sufficient to incorporate said antibiotic without substantive modification to said fiber matrices of said fabricated textile article such that said incorporated antibiotic retains its recognized antimicrobial activity and is sustainedly released from the fiber matrices over time.

2. The method for making an infection-resistant fabricated textile article as recited in claim 1 wherein said antibiotic is a fluoroquinolone.

3. The method for making an infection-resistant fabricated textile article as recited in claim 2 wherein said fluoroquinolone antibiotic is at least one selected from the group consisting of Ciprofloxacin, Ofloxacin, Norfloxacin, Sparfloxacin, Tomafloxacin, Enofloxacin, Lovafloxacin, Lomefloxacin, Pefloxacin, Fleroxacin, Avefloxin, and DU6859a.

4. The method for making an infection-resistant fabricated textile article as recited in claim 1 wherein said fiber matrix is comprised of at least one synthetic polymer material.

5. The method for making an infection-resistant fabricated textile article as recited in claim 4 wherein said fiber matrix is comprised of a synthetic polymer material selected from the group consisting of polyethylene terephthalate, nylon, polyurethane, polytetrafluoroethylene, polyglycolic acid, and mixtures of these polymers.

6. The method for making an infection-resistant fabricated textile article as recited in claim 1 wherein said fiber matrix comprises a naturally-occurring material.

7. The method for making an infection-resistant fabricated textile article as recited in claim 6 wherein said naturally-occurring material is selected from the group consisting of silk, cotton, linen, and wool.

8. The method for making an infection-resistant fabricated textile article as recited in claim 1 wherein said perfusing step further comprises the steps of:

employing a structured perfusion chamber of sufficient internal volume to contain the fabricated textile article; and delivering said prepared aqueous antibiotic fluid to said internal volume of said structured perfusion chamber for perfusion across said fiber matrices of said fabricated textile article.

9. The method for making an infection-resistant fabricated textile article as recited in claim 1 wherein said fabricated textile article is an implantable medical prosthesis.

10. The method for making an infection-resistant fabricated textile article as recited in claim 1 wherein said fabricated textile article is an implantable mechanical medical device.

11. The method for making an infection-resistant fabricated textile article as recited in claim 1 wherein said fabricated textile article is an implantable tubular conduit suitable for vascular graft applications.

12. The method for making an infection-resistant fabricated textile article as recited in claim 1 wherein said fabricated textile article is a wound treatment dressing.

13. The method for making an infection-resistant fabricated textile article as recited in claim 1 wherein said heating of said dried antibiotic perfused fabricated textile article further comprises exposing said perfused fabricated textile fabric to dry heat at an elevated temperature ranging from about 100–300° C.

14. The method for making an infection-resistant fabricated textile article as recited in claim 1 wherein said heating of said dried antibiotic perfused fabricated textile article further comprises:

immersing said dried antibiotic perfused fabricated textile fabric in a liquid dye bath of comparable antibiotic concentration; and heating said liquid dye bath and said immersed perfused fabricated textile fabric to an elevated temperature ranging from about 60–120 ° C.

* * * * *